(12) United States Patent
Peng et al.

(10) Patent No.: US 9,663,458 B2
(45) Date of Patent: May 30, 2017

(54) DIAMINOGUANIDINE DERIVATIVES AND APPLICATION THEREOF IN PREPARATION OF ANIMAL GROWTH PROMOTERS USED IN FEED

(71) Applicant: GUANGZHOU INSIGHTER BIOTECHNOLOGY CO., LTD., Luogang, Guangzhou, Guangdong (CN)

(72) Inventors: Xianfeng Peng, Guangzhou (CN); Zonghua Qin, Guangzhou (CN); Fang Li, Guangzhou (CN); Xiaolan Ye, Guangzhou (CN)

(73) Assignee: GUANGZHOU INSIGHTER BIOTECHNOLOGY CO., LTD., Guangzhou (CN)

( * ) Notice: Subject to any disclaimer, the term of this patent is extended or adjusted under 35 U.S.C. 154(b) by 0 days.

(21) Appl. No.: 15/114,025

(22) PCT Filed: Mar. 19, 2014

(86) PCT No.: PCT/CN2014/073702
§ 371 (c)(1),
(2) Date: Jul. 25, 2016

(87) PCT Pub. No.: WO2015/113321
PCT Pub. Date: Aug. 6, 2015

(65) Prior Publication Data
US 2016/0340299 A1 Nov. 24, 2016

(30) Foreign Application Priority Data
Jan. 29, 2014 (CN) .......................... 2014 1 0043200

(51) Int. Cl.
| | | |
|---|---|---|
| *C07C 281/18* | (2006.01) | |
| *A23K 20/111* | (2016.01) | |
| *A23K 50/75* | (2016.01) | |
| *A23K 50/30* | (2016.01) | |

(52) U.S. Cl.
CPC .......... *C07C 281/18* (2013.01); *A23K 20/111* (2016.05); *A23K 50/30* (2016.05); *A23K 50/75* (2016.05); *C07C 2101/08* (2013.01)

(58) Field of Classification Search
None
See application file for complete search history.

(56) References Cited

U.S. PATENT DOCUMENTS

| | | |
|---|---|---|
| 3,795,692 A | 3/1974 | Kulsa et al. |
| 3,901,944 A | 8/1975 | Tomcufcik |
| 3,973,039 A | 8/1976 | Livak et al. |
| 4,015,016 A | 3/1977 | Livak et al. |

FOREIGN PATENT DOCUMENTS

| | | |
|---|---|---|
| CN | 1093081 A | 10/1994 |
| GB | 1 304 164 A | 1/1973 |
| GB | 1 339 467 A | 12/1973 |
| JP | 54-95638 A | 7/1979 |
| WO | 02/12178 A1 | 2/2002 |

OTHER PUBLICATIONS

Database CAPLUS in STN, Acc. No. 2011:277570, Bose et al., Organic & Biomolecular Chemistry (2011), 9(6), pp. 1972-1979 (abstract).*
Database CAPLUS in STN, Acc. No. 1990:43357, Ampilogova et al., Zhurnal Analiticheskoi Khimii (1989), 44(4), pp. 620-623 (abstract).*
Bose et al., Organic & Biomolecular Chemistry (2011), 9(6), pp. 1972-1979.*
Lieber et al., "Alkylidene and Arylidene Derivatives of Diaminoguanidine" J. Org. Chem., Apr. 30, 1952, vol. 17, No. 4, pp. 518-522, (6 pages).
Scott et al., Polynitrogen Systems from Hydrazinocarbonic Acids. I. Diformazans J. Am. Chem. Soc., Nov. 5, 1953, vol. 75, No. 21, pp. 5309-5312, (5 pages).
International Search Report dated Sep. 26, 2014, issued in counterpart International Application No. PCT/CN2014/073702 (3 pages).

* cited by examiner

*Primary Examiner* — Brian J Davis
(74) *Attorney, Agent, or Firm* — Westerman, Hattori, Daniels & Adrian, LLP

(57) ABSTRACT

Diaminoguanidine derivatives in preparation of animal growth promoters used in feed. The diaminoguanidine derivatives have a structural formula as shown in formula (I), wherein $R_1$ is methyl, ethyl, isopropyl, n-butyl, n-propyl, n-pentyl, n-octyl, n-tetradecyl, sec-butyl, 3-pentyl, cyclopentyl or benzyl. The diaminoguanidine compounds significantly improve the productivity of ducks if they are fed with the diaminoguanidine compounds. Productivity of pigs or chickens is also improved with such diaminoguanidine compounds.

Formula (I)

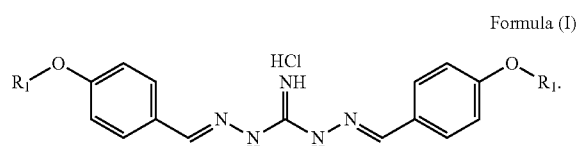

5 Claims, No Drawings

DIAMINOGUANIDINE DERIVATIVES AND APPLICATION THEREOF IN PREPARATION OF ANIMAL GROWTH PROMOTERS USED IN FEED

FIELD OF THE INVENTION

The present invention relates to the field of feed for poultry and livestock, specifically to diaminoguanidine derivatives and application thereof in preparation of an animal growth promoter used in feed.

BACKGROUND OF THE INVENTION

Growth promoters used in feed, which cover bioactive substances and preparations thereof with various effective mechanisms and various chemical structures, have contributed significantly to the improvement of feed conversion efficiency and productivity of pastoral industry. However, a great amount of antibiotic growth promoters have been or are about to be banned due to the transfer of drug resistance.

Therefore, it is an issue that how to screen out safe and efficient growth promoters used in feed, which are not for human medical use and exhibit no cross resistance with antibiotic for human use, especially non-antibiotic and non-hormonal growth promoters. And the present invention has solved this issue.

SUMMARY OF THE INVENTION

The first object of the present invention is to provide diaminoguanidine derivatives which can promote the growth of animals.

The diaminoguanidine derivatives of the present invention have a structural formula as shown in formula (I).

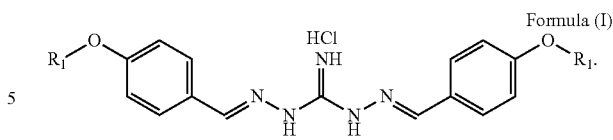

Wherein, $R_1$ is methyl, ethyl, isopropyl, n-butyl, n-propyl, n-pentyl, n-octyl, n-tetradecyl, sec-butyl, 3-pentyl, cyclopentyl or benzyl.

The second object of the present invention is to provide an application of the diaminoguanidine derivatives, which are as shown in formula (I), in preparation of animal growth promoters used in feed.

Said animal includes ducks, pigs, chickens, or the like, in all growth stages.

Dosage of the diaminoguanidine derivative in animal feeds is 0.1~200 ppm, and the feed can be complete formula feed.

The diaminoguanidine derivatives of the present invention as shown in formula (I) show low toxicity or non-toxicity to animals, which make it more suitable to be applied as a growth promoters used in feed and has a very good application prospect in cultivation industry.

Via feeding experiments, it has been discovered for the first time by the inventors that, productivity of ducks is improved significantly if they are fed with the diaminoguanidine compounds. It has also been discovered via feeding experiments that productivity of pigs or chickens is improved with such diaminoguanidine compounds.

DETAILED DESCRIPTION OF THE EMBODIMENTS

The present invention is described in farther detail with reference to embodiments which shall not be regarded as limits to the present invention.

Structural formulas and marks of the diaminoguanidine derivatives of the present invention are as shown below.

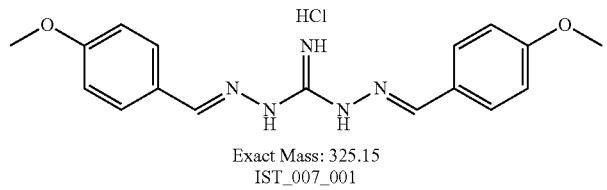

Exact Mass: 325.15
IST_007_001

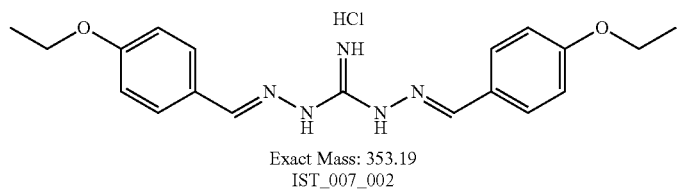

Exact Mass: 353.19
IST_007_002

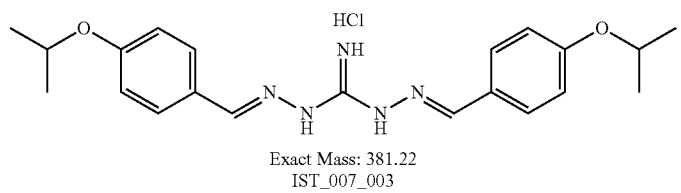

Exact Mass: 381.22
IST_007_003

-continued
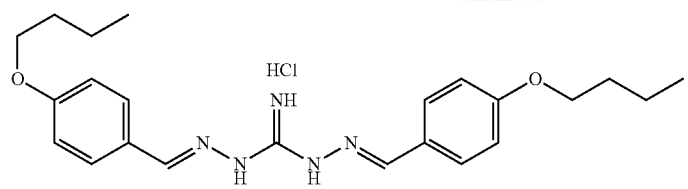
Exact Mass: 409.25
IST_007_005
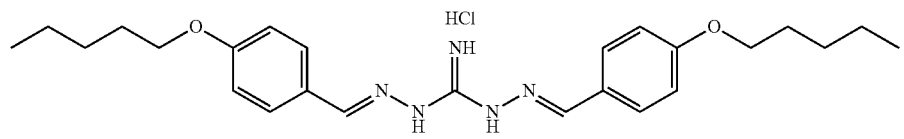
Exact Mass: 437.28
IST_007_019
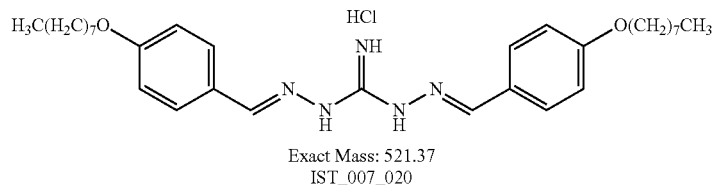
Exact Mass: 521.37
IST_007_020
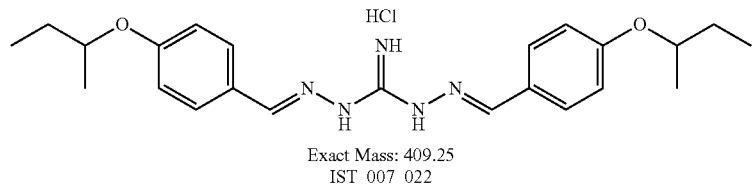
Exact Mass: 409.25
IST_007_022
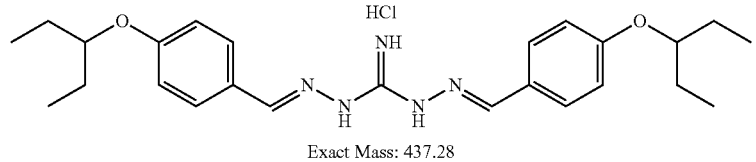
Exact Mass: 437.28
IST_007_023
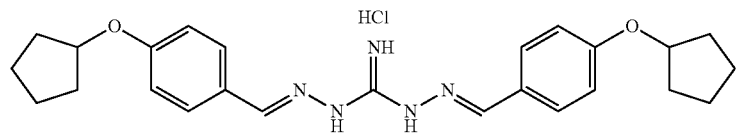
Exact Mass: 433.25
IST_007_024
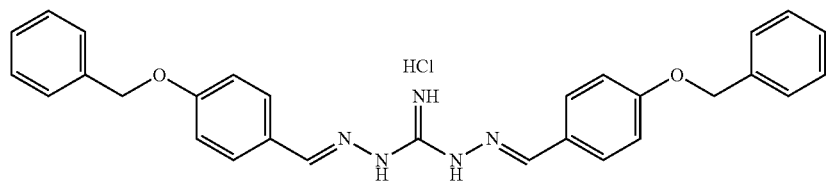
Exact Mass: 477.22
IST_007_025
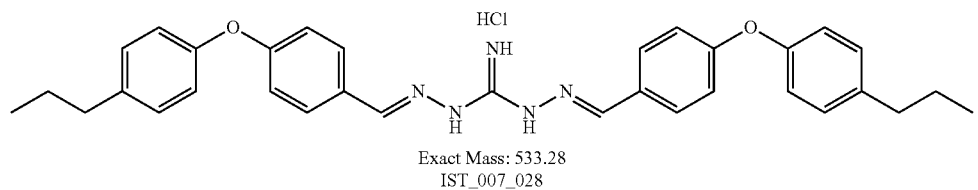
Exact Mass: 533.28
IST_007_028

Embodiment 1

Structural Formula

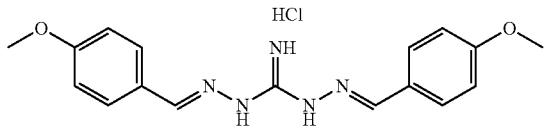

Preparation of 1,3-bis[(4-methoxybenzylidene)amino]guanidine hydrochloride (IST_007_001)

4-Methoxybenzaldehyde (30 g, 0.22 mol, 2 eq) was dissolved in about 300 ml of ethanol. Then the resulting solution was added with diaminoguanidine monohydrochloride (0.7~1.5 eq), refluxed until complete dissolution, and then reaction proceeded at a constant temperature for 1~5 hours with stirring until TLC (thin layer chromatography) showed that the 4-methoybenzaldehyde had been reacted completely. The solution was cooled to −10° C. with stirring to give a great amount of white precipitate, and then filtrated. Filter cake was washed with cold ethanol for 2~3 times, and subjected to rotary evaporation to remove the solvent and give a product, i.e., 1,3-bis[(4-methoxybenzylidene)amino]guanidine hydrochloride.

$^1$H-NMR: δH (DMSO, 500 MHz) 12.2 (2H, 5), 8.38 (4H, s), 7.88 (4H, d), 7.03 (4H, d), 3.8 (6H, s).

Embodiment 2

Structural Formula

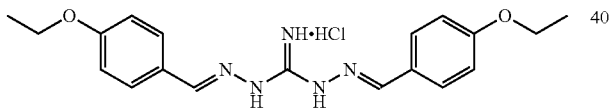

Preparation of 1,3-bis[(4-ethoxybenzylidene)amino]guanidine hydrochloride (IST_007_002)

4-Ethoxybenzaldehyde (24.77 g, 0.165 mol, 2 eq) was dissolved in about 300 ml of ethanol. Then the resulting solution was added with diaminoguanidine monohydrochloride (0.7~1.5eq), refluxed until complete dissolution, and then reaction proceeded at a constant temperature for 1~5 hours with stirring until TLC showed that the 4-ethoxybenzaldehyde had been reacted completely. The solution was cooled to −10° C. with stirring to give a great amount of white precipitate, and then filtrated. Filter cake was washed with cold ethanol for 2~3 times, and subjected to rotary evaporation to remove the solvent and give a product, i.e., 1,3-bis[(4-ethoxybenzylidene)amino]guanidine hydrochloride.

$^1$H-NMR: δH (DMSO, 500 MHz) 8.35 (4H, s), 7.86 (4H, d), 7.02 (4H, d), 4.1 (4H, m), 1.34 (6H, m).

Embodiment 3

Structural Formula

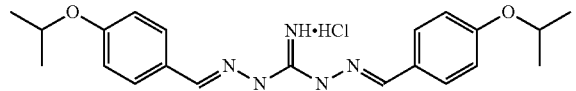

Preparation of 1,3-bis[(4-isopropoxybenzylidene)amino]guanidine hydrochloride (IST_007_003)

4-n-butoxybenzaldehyde (25 g, 0.153 mol, 2 eq) was dissolved in about 300 ml of ethanol. Then the resulting solution was added with diaminoguanidine monohydrochloride (0.7~1.5 eq), refluxed until complete dissolution, and then reaction proceeded at a constant temperature for 1~5 hours with stirring until TLC showed that the 4-isopropoxybenzaldehyde had been reacted completely. The solution was cooled to −10° C. with stirring to give a great amount of white precipitate, and then filtrated. Filter cake was washed with cold ethanol for 2~3 times, and subjected to rotary evaporation to remove the solvent and give a product, i.e., 1,3-bis[(4-isopropoxybenzylidene)amino]guanidine hydrochloride.

$^1$H-NMR: δH (DMSO, 500 MHz) 11.77 (2H, s), 8.29 (4H s), 7.85 (4H, d), 7.01 (4H, d), 4.72 (2H, m), 1.29 (12H, d).

Embodiment 4

Structural Formula

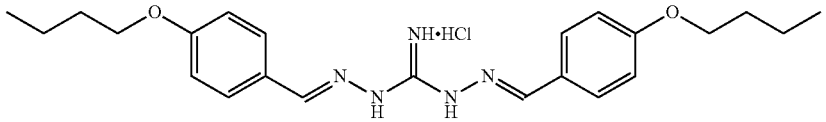

Preparation of 1,3-bis[(4-butoxybenzylidene)amino]guanidine hydrochloride (IST_007_005)

4-n-butoxylenzaldehyde (25 g, 0.14 mol, 2 eq) was dissolved in about 150 ml of ethanol. Then the resulting solution was added with diaminoguanidine monohydrochloride (0.7~1.5 eq), refluxed until complete dissolution, and then reaction proceeded at a constant temperature for 1~5 hours with stirring until TLC showed that the 4-n-butoxybenzaldehyde had been reacted completely. The solution was cooled to −10° C. with stirring to give a great amount of white precipitate, and then filtrated. Filter cake was washed with cold ethanol for 2~3 times, and subjected to rotary evaporation to remove the solvent and give a product, i.e., 1,3-bis[(4-butoxybenzylidene)amino]guanidine hydrochloride.

¹H-NMR: δH (DMSO, 500 MHz) 12.15 (2H, s), 8.38 (4H, d) 7.86 (4H, d), 7.02 (4H, d), 4.0 (4H, m), 1.7 (4H, m) 1.44 (4H, m), 0.93 (6H, m).

Embodiment 5

Structural Formula

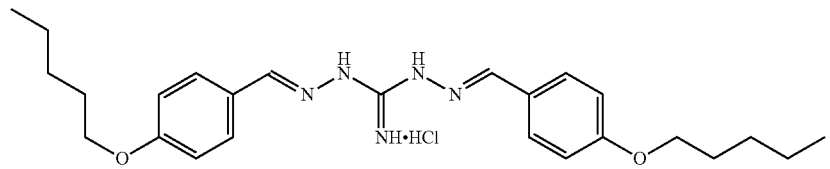

Preparation of 1,3-bis[(4-pentoxybenzylide)amino]guanidine hydrochloride (IST_007_019)

Step 1:
A mixture of 4-hydroxybenzaldehyde (12.2 g, 100 mmol, 1 eq), 1-bromopentane (0.8~1.5 eq) and potassium carbonate (1~3 eq) was added with 30 ml of DMF, and stirred at 50~100° C. for 5~16 hours, wherein TLC (PE:EA=5:1) gave a new spot with low polarity, and showed that a little amount of 4-hydroxybenzaldehyde had not been reacted. The resulting solution was cooled to room temperature, and then added with 100 ml of dichloromethane and 100 ml of water, and the layers were separated. The resulting organic phase was washed with water twice, dried over 20 g of anhydrous sodium sulfate for about 30 minutes, filtrated to remove the inorganic salt, and subjected to a gradient elution from 100% petroleum ether to petroleum ether/ethyl acetate (5:1) over a 200~300 mesh silica gel column to give pure 4-n-pentoxybenzaldehyde.

Step 2:
4-n-pentoxybenzaldehyde (15.36 g, 0.08 mol, 2 eq) was dissolved in about 150 ml of ethanol. Then the resulting solution was added with diaminoguanidine monohydrochimide (0.7~1.5 eq), stirred at 10~70° C. for 17 hours to give clear liquid. The liquid was subjected to rotary evaporation to remove the solvent, added into 150 ml of ethyl acetate, stirred at room temperature for 2~5 hours to give a great amount of precipitate, and then filtrated. The filter cake was washed with cold ethyl acetate (50 ml×3), and dried via rotary evaporation in a 40° C. water bath to give a product, i.e., 1,3-bis[(4-pentoxybenzylidene)amino]guanidine hydrochloride.

¹H-NMR: δH (DMSO, 500 MHz) 12.133 (2H, s), 8.350 (4H, s), 7.845-7.863 (4H, d, J=9), 7.003-7.021 (4H, d, J=9), 4.011-4.037 (4H, m), 1.700-1.756 (4H, m), 1.342-1.432 (8H, m), 0.89-0.092 (6H, m).

Embodiment 6

Structural Formula

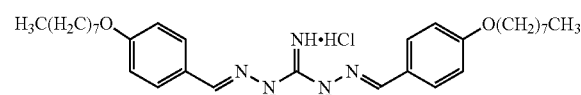

Preparation of 1,3-bis[(4-octoxybenzylidene)amino]guanidine hydrochloride (IST_007_020)

Step 1:
A mixture of 4-hydroxybenzaldehyde (12.2 g, 100 mmol, 1 eq), 1-bromooctane (0.8~1.5 eq) and potassium carbonate (1~3eq) was added with 30 ml of DMF, and stirred at 50~100° C. for 5~16 hours, wherein TLC (PE:EA=5:1) gave a new spot with low polarity, and showed that a little amount of 4-hydroxybenzaldehyde had not been reacted. The resulting solution was cooled to room temperature, and then added with 100 ml of dichloromethane and 100 ml of water, and the layers were separated. The resulting organic phase was washed with water twice, dried over 20 g of anhydrous sodium sulfate for about 30 minutes, filtrated to remove the inorganic salt, and subjected to a gradient elution from 100% petroleum ether to petroleum ether/ethyl acetate (5:1) over a 200~300 mesh silica gel column to give pure 4-n-octoxybenzaldehyde.

Step 2:
4-n-octoxybenzaldehyde (15.53 g, 0.045 mol, was dissolved in about 150 ml of ethanol. Then the resulting solution was added with diaminoguanidine monohydrochloride (0.7~1.5eq), stirred at 10~70° C. for 17 hours to give a great amount of white precipitate, and then filtrated. The filter cake was washed with ethanol (50 ml×3) for 2~3 times, and dried via rotary evaporation in a 40° C. water bath to give a product, i.e., 1,3-bis[(4-octoxybenzylidene)amino]guanidine hydrochloride.

¹H-NMR: δH (CDCl₃, 500 MHz) 12.411 (2H, s), 8.033 (2H, s), 7.532-7.547 (4H, d, J=7.5), 6.863-6.879 (4H, d, J=8), 6.675 (2H, s), 3.945-3.969 (4H, m), 1.750-1.805 (4H, m), 1.433-1.460 (4H, m), 1.289-1.340 (16H, m), 0.873-0.901 (6H, m).

Embodiment 7

Structural Formula

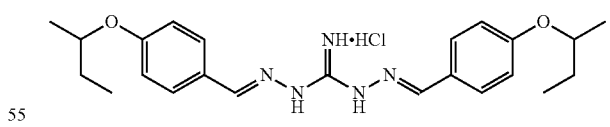

Preparation of 1,3-bis[(4-sec-butoxybenzylidene)amino]guanidine hydrochloride (IST_007_022)

Step 1:
A mixture of 4-hydroxybenzaldehyde (12.2 g, 100 mmol, 1 eq), 2-bromobutane (0.8~1.5 eq) and potassium carbonate (1~3 eq) was added with 30 ml of DMF, and stirred at 50~100° C. for 5~16 hours, wherein TLC (PE:EA=5:1) gave a new spot with low polarity, and showed that a little amount of 4-hydroxybenzaldehyde had not been reacted. The resulting solution was cooled to room temperature, and then added with 100 ml of dichloromethane and 100 ml of water, and the layers were separated. The resulting organic phase was washed with water twice, dried over about 20 g of anhydrous sodium sulfite for about 30 minutes, filtrated to remove the inorganic salt, and subjected to a gradient elution from 100% petroleum ether to petroleum ether/ethyl acetate (5:1) over a 200~300 mesh silica gel column to give pure 4-sec-butoxybenzaldehyde.

Step 2:

4-sec-butoxybenzaldehyde (14.24 g, 0.08 mol, 2 eq) was dissolved in about 150 ml of ethanol. Then the resulting solution was added with diaminoguanidine monohydrochloride (0.7~1.5 eq), and stirred at 10~70° C. for 17 hours. The diaminoguanidine monohydrochloride was dissolved gradually and no precipitate was observed. Then the solution was subjected to rotary evaporation in a 40° C. water bath to remove the solvent and thereby gave a residual as yellowish viscous solids. The solids were washed with about 200 ml of petroleum ether with stirring at room temperature for 2 hours to give a great amount of precipitate, and then filtrated. The filter cake was washed with petroleum ether (50 ml×2) for 2~3 times, and subjected to rotary evaporation to give a crude product. The crude product was washed with about 150 ml of ethyl acetate with stirring at room temperature for 3~5 hours, and then filtrated. The filter cake was washed with ethyl acetate (50 ml×2), then subjected to rotary evaporation to give a white solid product, i.e., 1,3-bis[(4-sec-butoxybenzylidene)amino]guanidine hydrochloride.

$^1$H-NMR: δH (CDCl$_3$, 500 MHz) 12.571 (2H, s), 8.071 (2H, s), 7.545-7.562 (4H, d, J=8.5), 6.875-6.892 (4H, d, J=8.5), 6.589 (2H, s), 4.333-4.367 (2H, m), 1.712-1.781 (2H, m), 1.610-1.679 (2H, m), 1.302-1.314 (6H, d, J=6), 0.961-0.991 (6H, m).

Embodiment 8

Structural Formula

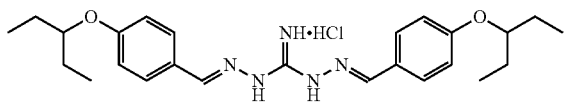

Preparation of 1,3-bis[[4-(3-pentoxy)benzylidene]amino]guanidine hydrochloride (IST_007_023)

Step 1:

A mixture of 4-hydroxybenzaldehyde (12.2 g, 100 mmol, 1 eq), 3-bromopentane (0.8~1.5 eq) and potassium carbonate (1~3 eq) was added with 30 ml of DMF, and stirred at 50~100° C. for 5~16 hours, wherein TLC (PE:EA=5:1) gave a new spot with low polarity, and showed that a little amount of 4-hydroxybenzaldehyde had not been reacted. The resulting solution was cooled to room temperature, and then added with 100 ml of dichloromethane and 100 ml of water, and the layers were separated. The resulting organic phase was washed with water twice, dried over about 20 g of anhydrous sodium sulfate for about 30 minutes, filtrated to remove the inorganic salt, and subjected to a gradient elution from 100% petroleum ether to petroleum ether/ethyl acetate (5:1) over a 200~300 mesh silica gel column to give pure 4-(3-pentoxy) benzaldehyde.

Step 2:

4-(3-Pentoxy)benzaldehyde (15.36 g, 0.08 mol, 2 eq) was dissolved in about 150 ml of ethanol. Then the resulting solution was added with diaminoguanidine monohydrochloride (0.7~1.5 eq), and stirred at 10~70° C. for 17 hours. The diaminoguanidine monohydrochloride was dissolved gradually and no precipitate was observed. Then the solution was subjected to rotary evaporation in a 40° C. water bath to remove the solvent and thereby gave a residual as yellowish viscous solids. The solids were washed with about 200 ml of petroleum ether with stirring at room temperature for 2 hours to give a great amount of precipitate, and then filtrated. The filter cake was washed with petroleum ether (50 ml×2) for 2~3 times, and subjected to rotary evaporation to give a crude product. The crude product was washed with about 150 ml of ethyl acetate with stirring at room temperature for 3~5 hours, and then filtrated. The filter cake was washed with ethyl acetate (50 ml×2), then subjected to rotary evaporation to give a white solid product, i.e., 1,3-bis[[4-(3-pentoxy)benzylidene]amino]guanidine hydrochloride.

$^1$H-NMR: δH (CDCl$_3$, 500 MHz) 12.514 (2H, s), 8.075 (2H, 7.545-7.561 (4H, d, J=8), 6.884-6.901 (4H, d, J=8.5), 6.593 (2H, s), 4.162-4.184 (2H, m), 1.664-1.719 (8H, m), 0.940-0.970 (12H, m).

Embodiment 9

Structural Formula

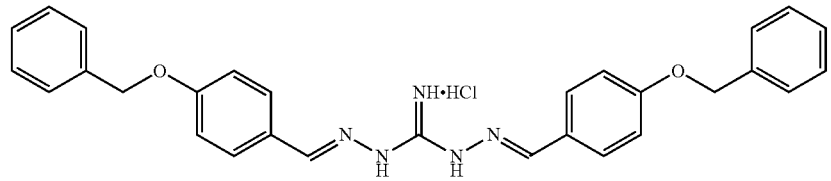

Preparation of 1,3-bis[(4-benzyloxybenzylidene)amino]guanidine hydrochloride (IST_007_025)

Step 1:

A mixture of 4-hydroxybenzaldehyde (6.1 g, 50 mmol, 1 eq), benzyl bromide (0.8~1.5 eq) and potassium carbonate (1~3 eq) was added with 30 ml of DMF, and stirred at 50~100° C. for 5~16 hours, wherein TLC (PE:EA=5:1) gave a new spot with low polarity, and showed that a little amount of 4-hydroxybenzaldehyde had not been reacted. The resulting solution was cooled to room temperature, and then added with 100 ml of dichloromethane and 100 ml of water, and the layers were separated. The resulting organic phase was washed with water twice, dried over about 20 g of anhydrous sodium sulfate for about 30 minutes, filtrated to remove the inorganic salt, and subjected to a gradient elution from 100% petroleum ether to petroleum ether/ethyl acetate (5:1) over a 200~300 mesh silica gel column to give pure 4-benzyloxybenzaldehyde.

Step 2:

4-Benzyloxybenzaldehyde (9.75 g, 46 mmol, 2 eq) was dissolved in about 150 ml of ethanol. Then the resulting solution was added with diaminoguanidine monohydrochloride (0.7~1.5 eq), stirred at 10~70° C. for 17 hours to give a great amount of white precipitate while the diaminoguanidine monohydrochloride was dissolved gradually, and then filtrated. The filter cake was washed with ethanol (50 ml×2), and dried via rotary evaporation in a 40° C. water bath to give a product, i.e., 1,3-bis[(4-benzyloxybenzylidene)amino]guanidine hydrochloride.

$^1$H-NMR: δH (DMSO, 500 MHz) 12.013 (2H, s), 8.338 (4H, s), 7.872-7.889 (4H, d, J=8.5), 7.467-7.481 (4H, d, J=7), 7.393-7.423 (4H, m), 7.333-7.362 (2H, m), 7.110-7.128 (4H, m, J=9), 5.184 (4H, s).

Embodiment 10

Structural Formula

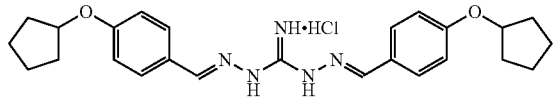

Preparation of
1,3-bis[(4-cyclopentoxybenzylidene)amino]guanidine hydrochloride (IST_007_024)

Step 1:

A mixture of 4-hydroxybenzaldehyde (12.2 g, 100 mmol, 1 eq), cyclopentyl bromide (0.8~1.5 eq) and potassium carbonate (1~3 eq) was added with 30 ml of DMF, and stirred at 50~100° C. for 5~16 hours, wherein TLC (PE:EA=5:1) gave a new spot with low polarity, and showed that a little amount of 4-hydroxybenzaldehyde had not been reacted. The resulting solution was cooled to room temperature, and then added with 100 ml of dichloromethane and 100 ml of water, and the layers were separated. The resulting organic phase was washed with water twice, dried over about 20 g of anhydrous sodium sulfate for about 30 minutes, filtrated to remove the inorganic salt, and subjected to a gradient elution from 100% petroleum ether to petroleum ether/ethyl acetate (5:1) over a 200~300 mesh silica gel column to give pure 4-cyclopentoxybenzaldehyde.

Step 2:

4-Cyclopentoxybenzaldehyde (15.2 g, 0.08 mol, 2 eq) was dissolved in about 150 ml of ethanol. Then the resulting solution was added with diaminoguanidine monohydrochloride (0.7~1.5 eq), stirred at 10~70° C. for 17 hours to give a great amount of white precipitate while the diaminoguanidine monohydrochloride was dissolved gradually, and then filtrated. The filter cake was washed with ethanol (50 ml×2), and dried via rotary evaporation in a 40° C. water bath to give a product, i.e., 1,3-bis[(4-cyclopentoxybenzylidene)amino]guanidine hydrochloride.

$^1$H-NMR: δH (CDCl$_3$, 500 MHz) 12.428 (2H, s), 8.048 (2H, s), 7.524-7.538 (4H, d, J=7), 6.844-6.858 (4H, d, J=7), 6.677 (2H, m), 4.768 (2H, m), 1.798-1.912 (14H, m), 1.629 (2H, m).

Embodiment 11

Structural Formula

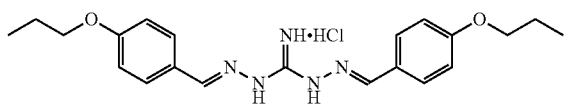

Preparation of
1,3-bis[(4-propoxybenzylidene)amino]guanidine hydrochloride (IST_007_028)

Step 1:

A mixture of 4-hydroxybenzaldehyde (12.2 g, 100 mol, 1 eq), 1-bromopropane 0.8~1.5 eq) and potassium carbonate (1~3 eq) was added with 30 ml of DMF, and stirred at 50~100° C. for 5~16 hours, wherein TLC (PE:EA=5:1) gave a new spot with low polarity and showed that a little amount of 4-hydroxybenzaldehyde had not been reacted. The resulting solution was cooled to room temperature, and then added with 100 ml of dichloromethane and 100 ml of water, and the layers were separated. The resulting organic phase was washed with water twice, dried over about 20 g of anhydrous sodium sulfate for about 30 minutes, filtrated to remove the inorganic salt, and subjected to a gradient elution from 100% petroleum ether to petroleum ether/ethyl acetate (5:1) over a 200~300 mesh silica gel column to give pure 4-propoxybenzaldehyde.

Step 2:

4-Propoxybenzaldehyde (12.4 g, 0.09 mol, 2 eq) was dissolved in about 150 ml of ethanol. Then the resulting solution was added with diaminoguanidine monohydrochloride (0.7~1.5 eq), stirred at 10~70° C. for 17 hours to give a great amount of white precipitate while the diaminoguanidine monohydrochloride was dissolved gradually, and then filtrated. The filter cake was washed with ethanol (50 ml×2), and dried via rotary evaporation in a 40° C. water bath to give a product, 1,3-bis[(4-propoxybenzylidene)amino]guanidine hydrochloride.

$^1$H-NMR: δH (CDCl$_3$, 500 MHz) 12.541 (2H, s), 8.085 (2H, s), 7.562-7.577 (4H, d, J=7.5), 6.897-6.913 (4H, d, J=8), 6.571 (2H, s), 3.953 (4H, m), 1.805-1.845 (4H, m), 1.033-1.062 (6H, m).

Embodiment 12: Minimum Inhibitory Concentration Against *Clostridium* Perfringens In Vitro (MICs, Ppm)

TABLE 1

Minimum inhibitory concentration of diaminoguanidine derivatives against *clostridium perfringens* in vitro

| Sample | CP-JM-1210-B | CP-JM-1210-E | CP-JM-1208-H |
|---|---|---|---|
| IST_007_001 | 1.56 | 50 | 12.5 |
| IST_007_003 | 3.13 | 12.5 | 12.5 |
| IST_007_002 | 0.2 | >100 | >100 |
| IST_007_005 | 0.78 | 25 | 12.5 |
| IST_007_019 | >200 | >200 | >200 |
| IST_007_020 | >200 | >200 | >200 |
| IST_007_022 | 12.5 | 12.5 | 12.5 |
| IST_007_023 | 12.5 | 12.5 | 12.5 |
| IST_007_024 | 1.56 | 3.13 | 1.56 |
| IST_007_025 | 100 | >200 | >200 |
| IST_007_028 | 1.56 | 1.56 | 1.56 |

Embodiment 13: Minimum Inhibitory Concentration Against Riemerella Anatipestifer In Vitro (MICs, Ppm)

TABLE 2

Minimum inhibitory concentration of diaminoguanidine derivatives against *riemerella anatipestifer* in vitro

| Sample | RA-HN-1211-C | RA-FS-1308-1 | RA-GD-1211-D |
|---|---|---|---|
| IST_007_001 | 3.13 | 6.25 | 3.13 |
| IST_007_003 | 1.56 | 1.56 | 1.56 |
| IST_007_002 | >100 | >100 | >100 |
| IST_007_005 | 1.56 | 1.56 | 1.56 |
| IST_007_019 | >200 | >200 | 0.39 |
| IST_007_020 | >200 | >200 | >200 |
| IST_007_022 | 1.56 | 1.56 | 0.2 |
| IST_007_023 | 1.56 | 1.56 | 0.78 |
| IST_007_024 | 0.39 | 0.39 | 0.78 |
| IST_007_025 | >200 | >200 | 0.39 |
| IST_007_028 | 0.39 | 1.56 | 0.39 |

Embodiment 14: Feeding Trial (Ducks)

800 1-day-old cherry valley ducks were divided into 8 groups, 100 ducks in each group. The ducks were fed with food and water ad libitum for 30 days, each group being fed with the same basal diet mixed with different compound of the IST_007 series, and productivity and survival rate of the ducks were obtained. Table 3 shows the grouping and dosages, and table 4 shows the productivity. The compounds of IST_007 series can substantially enhance the productivity of the ducks, concluded from the results.

TABLE 3

Grouping of the ducks of the IST_007_series, and dosages of additives

| Group | Compound | Dosage (ppm) |
|---|---|---|
| 1 | — | 0 |
| 2 | IST_007_028 | 20 |
| 3 | IST_007_001 | 20 |
| 4 | IST_007_022 | 20 |
| 5 | IST_007_023 | 20 |
| 6 | IST_007_003 | 20 |
| 7 | IST_007_005 | 20 |
| 8 | IST_007_024 | 20 |

TABLE 3-continued

TABLE 4

Feeding trial results of the IST_007_series compounds in ducks

| Group | Average initial weight | Average weight gain | Average feed conversion efficiency | Survival rate (%) |
|---|---|---|---|---|
| 1 | 51.6 | 55.8 | 2.16 | 100 |
| 2 | 51.6 | 61.6 | 2.04 | 100 |
| 3 | 51.6 | 62.1 | 2.01 | 100 |
| 4 | 51.6 | 61.3 | 2.08 | 100 |
| 5 | 51.6 | 62.4 | 2.05 | 100 |
| 6 | 51.6 | 63.6 | 2.03 | 100 |
| 7 | 51.6 | 62.4 | 2.07 | 100 |
| 8 | 51.6 | 63.1 | 2.09 | 100 |

Embodiment 15: Feeding Trial (Broilers)

400 1-day-aged, healthy, fast-grown yellow feather broilers (female) in the same growing state and similar in weight were randomly divided into eight groups according to table 5, 50 broilers in each group. Broilers in each group were fed with different dosage of the IST_007 series compounds. The broilers were kept in cages and fed with food and water ad libitum for 30 days, wherein weight gain and feed conversion efficiency of the broilers fed with IST_007 series compounds had been significantly improved (table 6).

TABLE 5

Grouping of the animals, and dosages of additives

| Group | Compound | Dosage (ppm) |
|---|---|---|
| 1 | — | 0 |
| 2 | — | 0 |
| 3 | IST_007_001 | 20 |
| 4 | IST_007_001 | 20 |
| 5 | IST_007_003 | 20 |
| 6 | IST_007_003 | 20 |
| 7 | IST_007_005 | 20 |
| 8 | IST_007_005 | 20 |

—: control blank, wherein IST_007 series compounds were not added

TABLE 6

Feeding trial results of the IST_007_series compounds in broilers

| Group | Initial weight (g) | Survival rate (%) | Average weight gain (g) | Consumption (kg) | Average daily weight gain (g) | Feed conversion efficiency |
|---|---|---|---|---|---|---|
| 1 | 39.7 | 100 | 713 | 76.6 | 23.7 | 2.15 |
| 2 | 38.5 | 100 | 712 | 75.2 | 23.7 | 2.11 |
| 3 | 39.8 | 100 | 764 | 71.7 | 25.5 | 1.88 |
| 4 | 39.1 | 100 | 775 | 73.8 | 25.8 | 1.91 |
| 5 | 39 | 100 | 791 | 73.7 | 26.3 | 1.86 |
| 6 | 39.6 | 100 | 795 | 72.3 | 26.5 | 1.82 |
| 7 | 39.4 | 100 | 796 | 74.1 | 26.5 | 1.86 |
| 8 | 40.2 | 100 | 787 | 72.5 | 26.2 | 1.84 |

Embodiment 16: Feeding Trial (Pigs)

90 65-day-aged. Duroc-YorkShire-Landrace crossbred lean pigs similar in weight were randomly divided into six groups, 15 pigs in each group. Pigs in each group were fed with the IST_007_series compounds with the dosages listed in table 7. The pigs were fed with food and water ad libitum for 14 days, wherein weight gain and feed conversion efficiency of the pigs fed with IST_007 series compounds had been significantly improved. Grouping and results of the trial were as shown in table 7 and table 8.

TABLE 7

Grouping of the animals, and dosages of additives

| Group | Quantity of the pigs | Compound | Dosage (mg/kg) | Administration |
|---|---|---|---|---|
| 1 | 15 | — | — | — |
| 2 | 15 | — | — | — |
| 3 | 15 | IST_007_003 | 25 | Mixed with feed |
| 4 | 15 | IST_007_003 | 25 | Mixed with feed |
| 5 | 15 | IST_007_028 | 25 | Mixed with feed |
| 6 | 15 | IST_007_028 | 25 | Mixed with feed |

—: control blank, wherein neither IST_007_003 nor IST_007_028 was added

TABLE 8

Feeding trial results of the IST_007_series compounds in pigs

| Group | Average initial weight (kg) | Average weight gain (kg) | Average daily weight gain (kg/day) | Consumption (kg) | Feed conversion efficiency |
|---|---|---|---|---|---|
| 1 | 15.7 | 6.2 | 0.44 | 198.3 | 2.13 |
| 2 | 16.2 | 6.1 | 0.43 | 192.9 | 2.11 |
| 3 | 16.3 | 7.8 | 0.56 | 215.3 | 1.84 |
| 4 | 15.4 | 8.2 | 0.58 | 203.4 | 1.65 |
| 5 | 15.3 | 7.7 | 0.55 | 201.3 | 1.75 |
| 6 | 16.4 | 7.3 | 0.52 | 202.5 | 1.85 |

The invention claimed is:

1. Diaminoguanidine derivatives, having a structural formula as shown in formula (I):

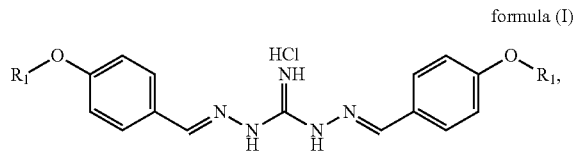

formula (I)

wherein, $R_1$ is ethyl, isopropyl, n-butyl, n-propyl, n-pentyl, n-tetradecyl, sec-butyl, 3-pentyl, cyclopentyl or benzyl.

2. A method of using diaminoguanidine derivatives in preparation of animal growth promoters comprising a step of adding the diaminoguanidine derivatives to animal feed, wherein the diaminoguanidine derivatives have a structural formula as shown in formula (I):

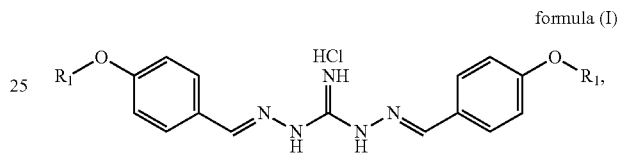

formula (I)

and R1 is methyl, ethyl, isopropyl, n-butyl, n-propyl, n-pentyl, n-octyl, n-tetradecyl, sec-butyl, 3-pentyl, cyclopentyl or benzyl.

3. The method according to claim 2, wherein the animal is a farm animal in all growth stages.

4. The method according to claim 3, wherein the farm animal is a duck, pig or chicken.

5. The method according to claim 2, wherein a concentration of the diaminoguanidine derivatives in animal feed is 0.1~200 ppm.

* * * * *